US00PP34952P3

(12) United States Plant Patent
Tufaro

(10) Patent No.: US PP34,952 P3
(45) Date of Patent: Jan. 31, 2023

(54) STRAWBERRY PLANT NAMED 'NSG 9'

(50) Latin Name: ***Fragaria x ananassa* Duchesne**
Varietal Denomination: NSG 9

(71) Applicant: Nova Siri Genetics SRL, Policoro (IT)

(72) Inventor: Nicola Tufaro, Nova Siri (IT)

(73) Assignee: NOVA SIRI GENETICS SRL, Policoro (IT)

( * ) Notice: Subject to any disclaimer, the term of this patent is extended or adjusted under 35 U.S.C. 154(b) by 0 days.

(21) Appl. No.: 17/832,168

(22) Filed: Jun. 3, 2022

(65) Prior Publication Data

US 2022/0394900 P1 Dec. 8, 2022

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./156, 208, 209
See application file for complete search history.

*Primary Examiner* — Karen M Redden
(74) *Attorney, Agent, or Firm* — Buchanan Ingersoll & Rooney P.C.

(57) ABSTRACT

A new and distinct variety of strawberry plant, referred to by its cultivar name, 'NSG 9', is provided which exhibits a semi-dense habit and an upright growth. 'NSG 9' displays, on an early basis, white inflorescence generally at a level above the foliage. 'NSG 9' commonly displays a calyx that is larger than the diameter of its corolla when open. 'NSG 9' forms in abundance early-ripening attractive fruits of large dimensions, longer in length than in width, mainly conical, with very firm flesh and orange red color. The new variety is particularly well suited for the commercial industry.

12 Drawing Sheets

Figure 1:
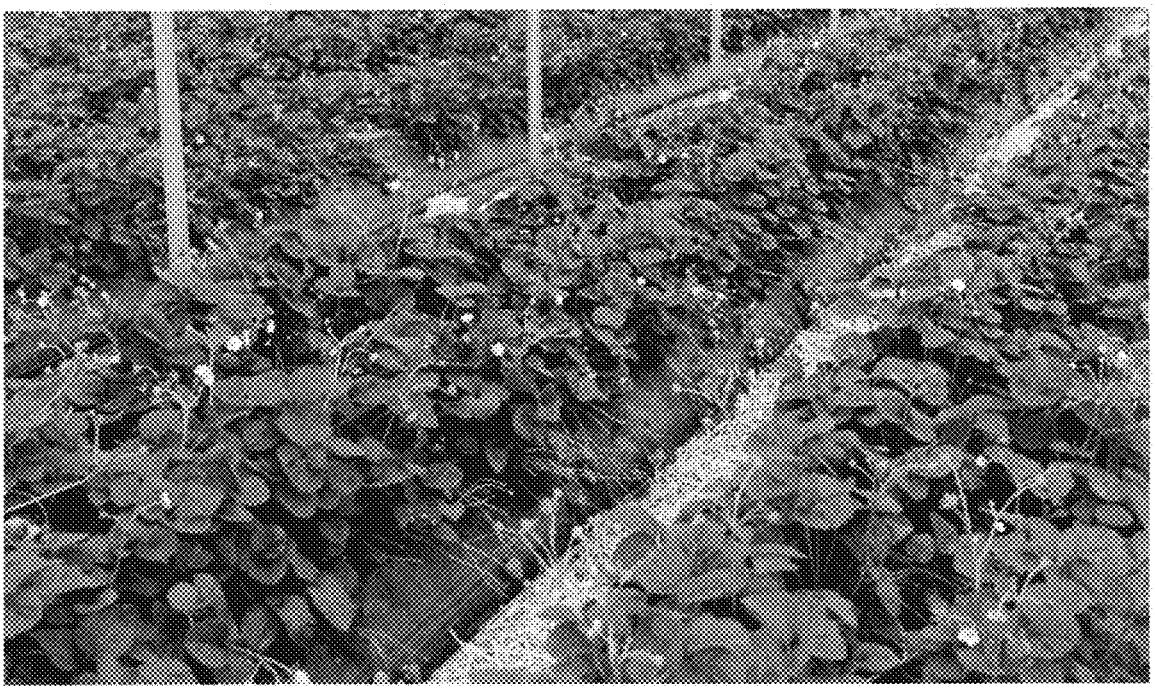

Botanical/commercial classification:
Latin name: *Fragaria* x *ananassa* Duchesne.
Varietal denomination: 'NSG 9'.

CROSS-REFERENCE TO RELATED APPLICATIONS

This application claims priority to Community Plant Variety Rights Application Number 2021/1460 which was filed in European Union through Community Plant Variety Office on Jun. 7, 2021, of which the content of is hereby expressly incorporated by reference in its entirety for all purposes.

SUMMARY OF THE INVENTION

The new and distinct short-day strawberry plant variety of the present invention was the product of a controlled breeding program that was carried out in Policoro (MT) Italy located at 40° 197 N-16° 656 E, wherein two parents were crossed which previously had been studied in the hope that they would contribute the desired characteristics. The female parent (i.e., the seed parent) was the 'NSG 203' variety (U.S. Plant Pat. No. 32,162 P3 and European Union Community Plant Variety Rights No. 57090), which is a strawberry variety plant with early-season ripening, high yield-season and produces fruit with high consistence and shelf life. The male parent (i.e., pollen parent) was the 'SIRIS' variety (non-patented in the United States and European Union Community Plant Variety Rights No. 34843) which is a strawberry variety plant with medium late-season yield and produces fruit with very high contents of sugar and exhibits high tolerance to infection by fungus, such as *Phytophthora cactorum* and *Colletotrichum acutatum*.

The parentage can be summarized as follows:

'NSG 203' x 'SIRIS'.

The seeds resulting from the above pollination were sown and small plants were obtained which were physically different from each other. Selective study and testing resulted in the identification of a single short-day strawberry plant of the new variety.

It was found that the new strawberry plant of the present invention possesses the following combination of characteristics:

(a) exhibits a semi-dense habit and an upright growth,
(b) displays, on an early basis, white inflorescence, generally, at a level above the foliage,
(c) commonly displays a calyx that is larger than the diameter of the corolla when open,
(d) forms in abundance early-ripening attractive fruits of large dimensions, longer in length than in width, mainly conical, with very firm flesh and orange red color.

The new variety well meets the needs of the horticultural industry. The new variety possesses characteristics that commonly are sought by commercial strawberry growers. For example, the new variety provides uniform attractive firm medium red, medium- ripening fruit in good yields. The new variety requires an induction period for flowering. This may be achieved by growing in a colder climate away from the equator or at a higher altitude above sea level.

The new variety can be readily distinguished from its ancestors. More specifically, the 'NSG 203' variety (i.e., the seed parent) generally displays a conical shape fruit, with a cavity that is either absent or small. The fruit of 'NSG 203' is much longer in length than width, with a very small difference between the terminal fruits and the others, has sepals which are disposed outward and a calyx diameter that is commonly slightly bigger in relation to the diameter of its fruit. On the contrary, the new variety has fruit which is still conical but possesses a medium cavity. The fruit of the new variety is also moderately longer in length than width, has a moderate difference between the terminal fruits and the others, possesses sepals which are disposed upward and has a calyx diameter that is almost equal to the diameter of its fruit. The leaf of 'NSG 203' is moderately longer in length than width and has an acute base. The new variety has a leaf with equal length and width and a rounded base. In addition, the variety "SIRIS" (i.e., the pollen parent) generally has medium leaves with medium green color, longer in width than length, with obtuse base. The new variety has bigger leaves with a lighter green, equal in length and width, with rounded base. The "SIRIS" variety shows cordate shape fruits, with the diameter of the calyx being much smaller when compared to diameter of the fruit, which has an absent or very small cavity. The fruit of the new variety; however, is conical, has a calyx diameter equal to the diameter of the fruit, and has a medium cavity.

Moreover, the new variety can be readily distinguished from non-parental related similar varieties. For example, the 'NSG 120' variety (U.S. Plant Pat. No. 32,192 P3 and European Union Community Plant Variety Rights No. 57092) shows medium to large leaves, moderately longer in length than width, with an acute base. The leaves of the new variety are big, almost equal in length and width, have a rounded base, are more wrinkled and are a lighter green color. In addition, the 'NSG 120' variety has conical, slightly rhomboidal fruit with a medium red color and the diameter of its calyx is slightly bigger than the diameter of its fruit. The new variety has conical fruit, with a red orange color and the diameter of its calyx is almost equal to the diameter of its fruit.

The new variety has been found to undergo asexual propagation in Spain and Italy by a number of routes, including by use of stolons and in vitro tissue culture. Specifically, the new variety has been asexually reproduced in a nursery setting by the use of stolons in Tordesillas, Spain, located at 41° 494 N-4° 908 E and in Policoro, Italy, by in vitro tissue culture. No rotting problems were observed on the roots during cultivation. The combination of characteristics exhibited by the new variety has been found to be stable and reliably transmitted to succeeding generations following such asexual reproduction. Accordingly, the new variety undergoes asexual propagation in a true-to-type manner by such asexual reproduction.

BRIEF DESCRIPTION OF THE PHOTOGRAPHS

The accompanying photographs show, as nearly true as it is reasonably possible to make the same in color illustrations of this character, typical specimens of the new variety identified by the code c20.v.17-9 (breeder reference). The illustrated strawberry plants of the new variety were asexually reproduced by stolons in a nursery at Tordesillas, Spain, 41° 494 N-4° 908 E , and were planted under the cover of plastic tunnels during mid October 2021 in Policoro (MT) located at 40° 197 N-16° 656 E, Italy.

FIG. 1—illustrates a row of fruiting plants in May 2022, wherein the level of the flowering is above the foliage.

Figure 2:
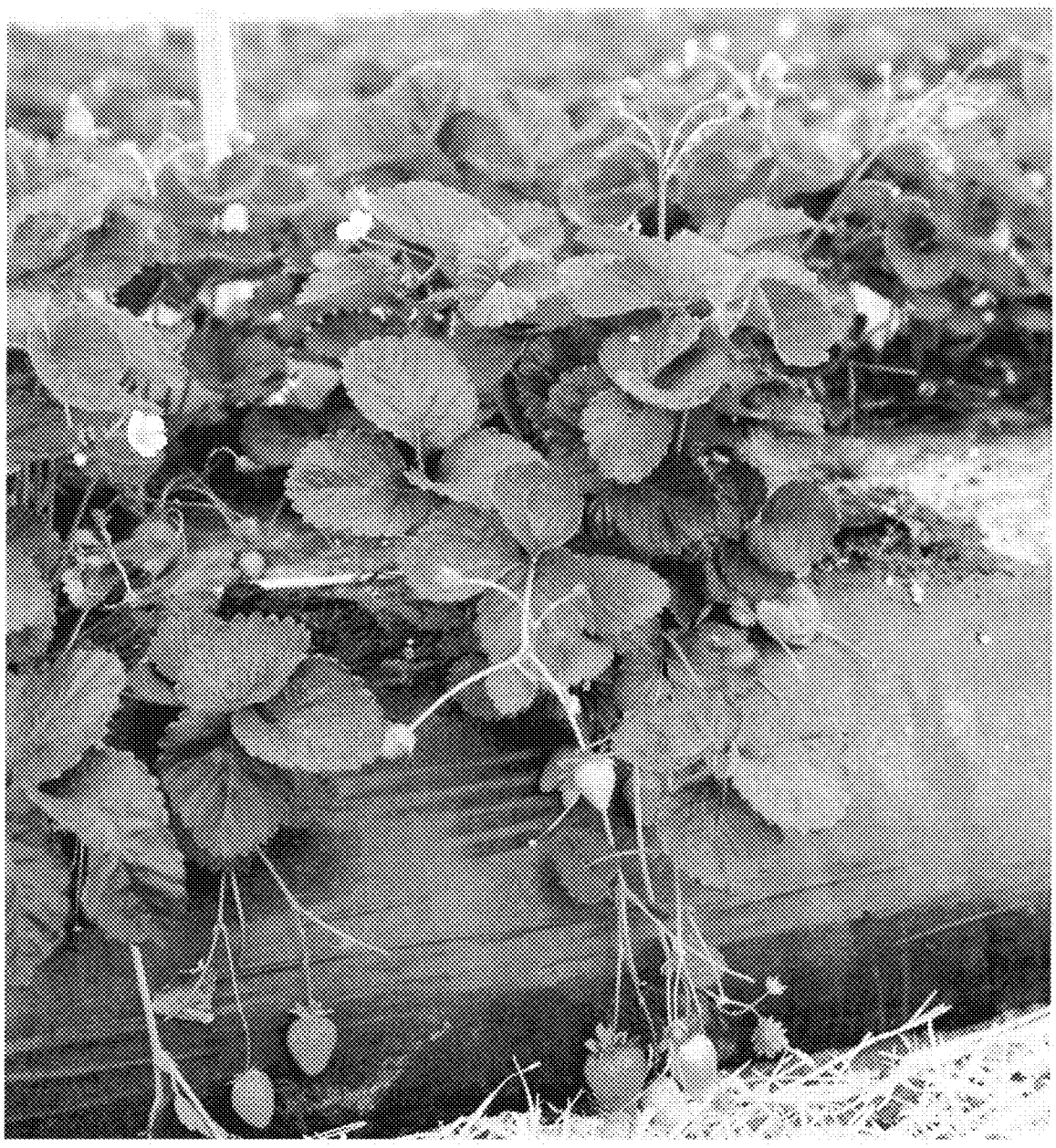

FIG. 2—illustrates the new plant variety with its upright habit and medium vigor.

Figure 3:
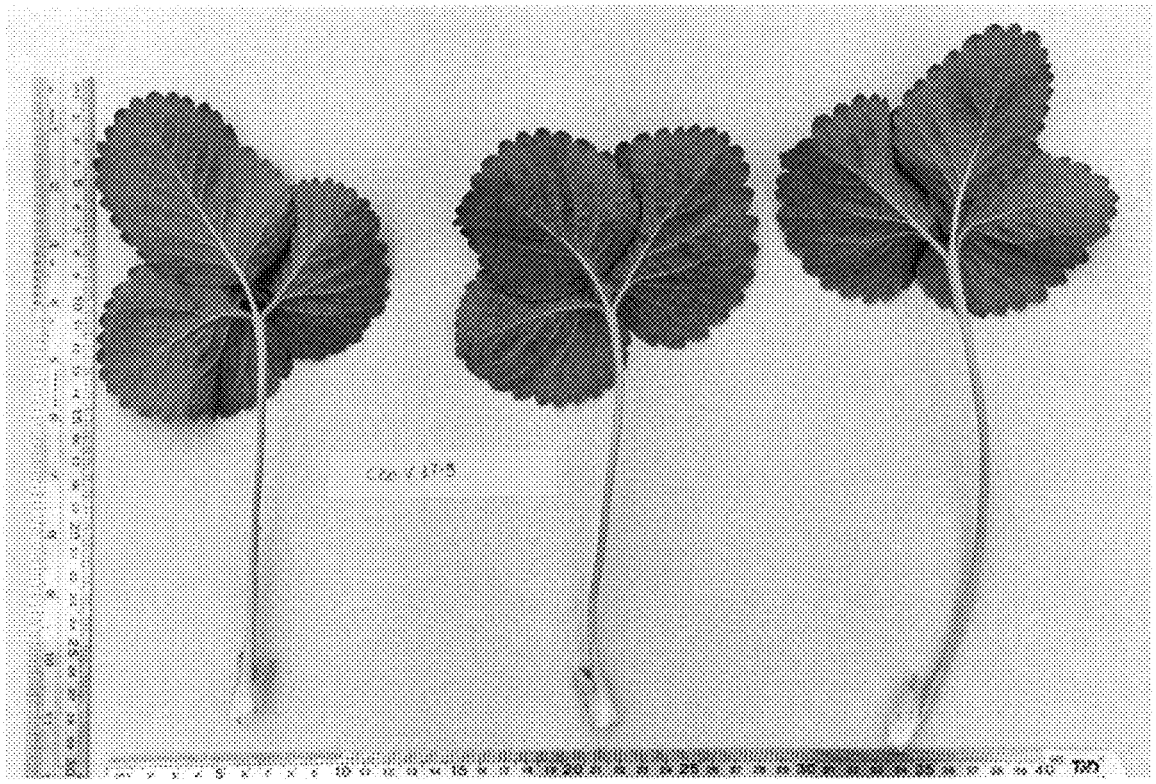

FIG. 3—illustrates specimens of the new variety's three-leaflet leaves—under surface, wherein the petiole and stipules are further apparent. Dimensions in centimeters and inches are included.

Figure 4:
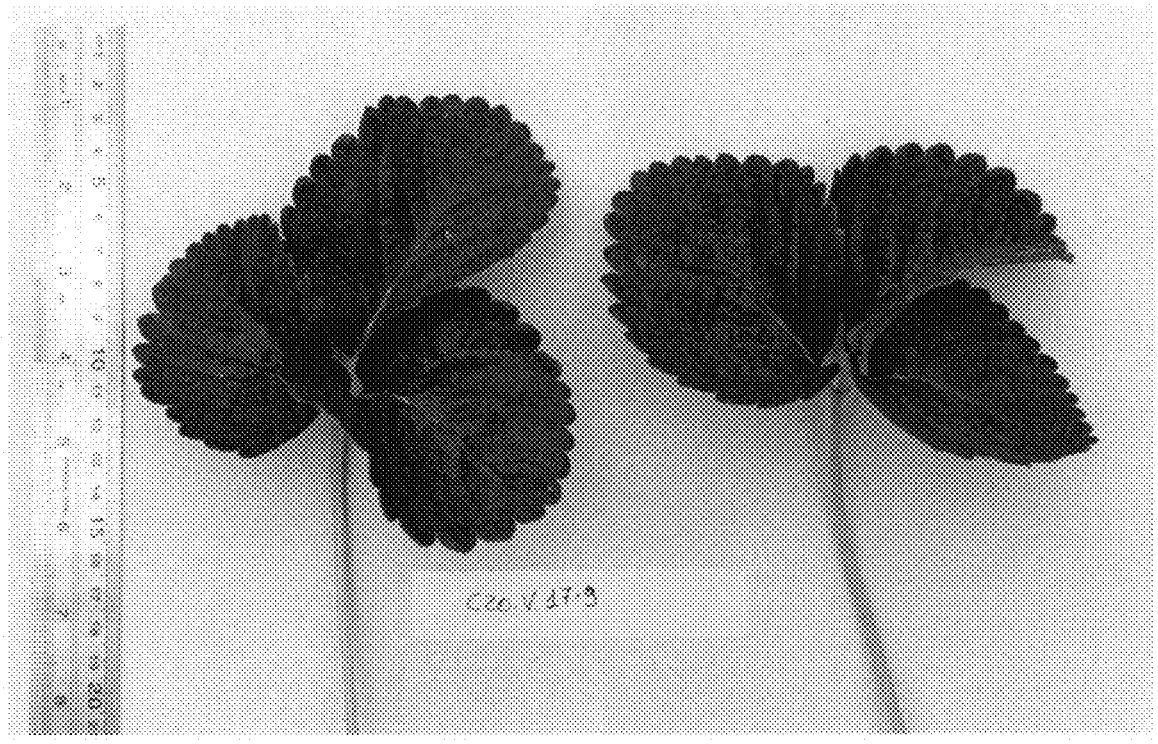

FIG. 4—illustrates specimens of the new variety's three-leaflet leaves—upper surface. Dimensions in centimeters and inches are included.

Figure 5:
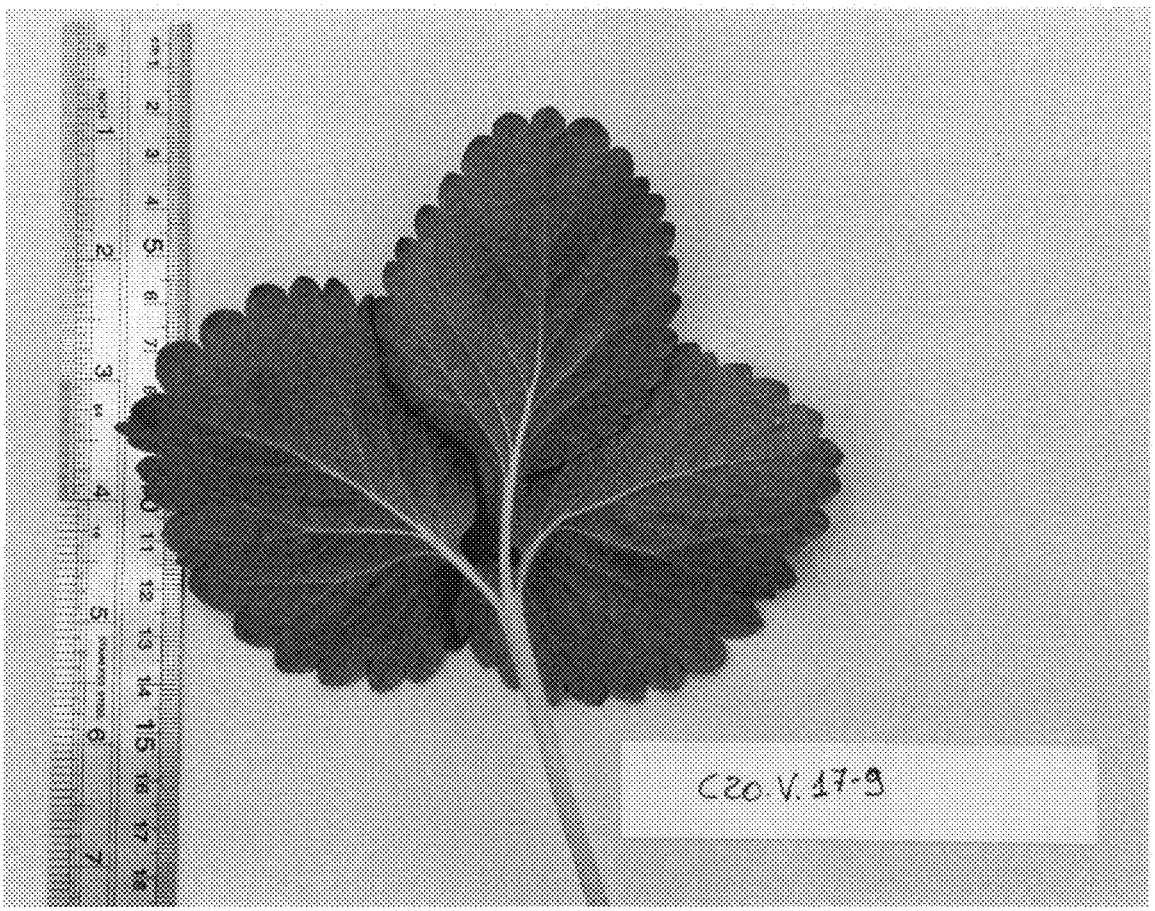

FIG. 5—illustrates the under surface of the new variety's terminal leaflet and its venature.

Figure 6:
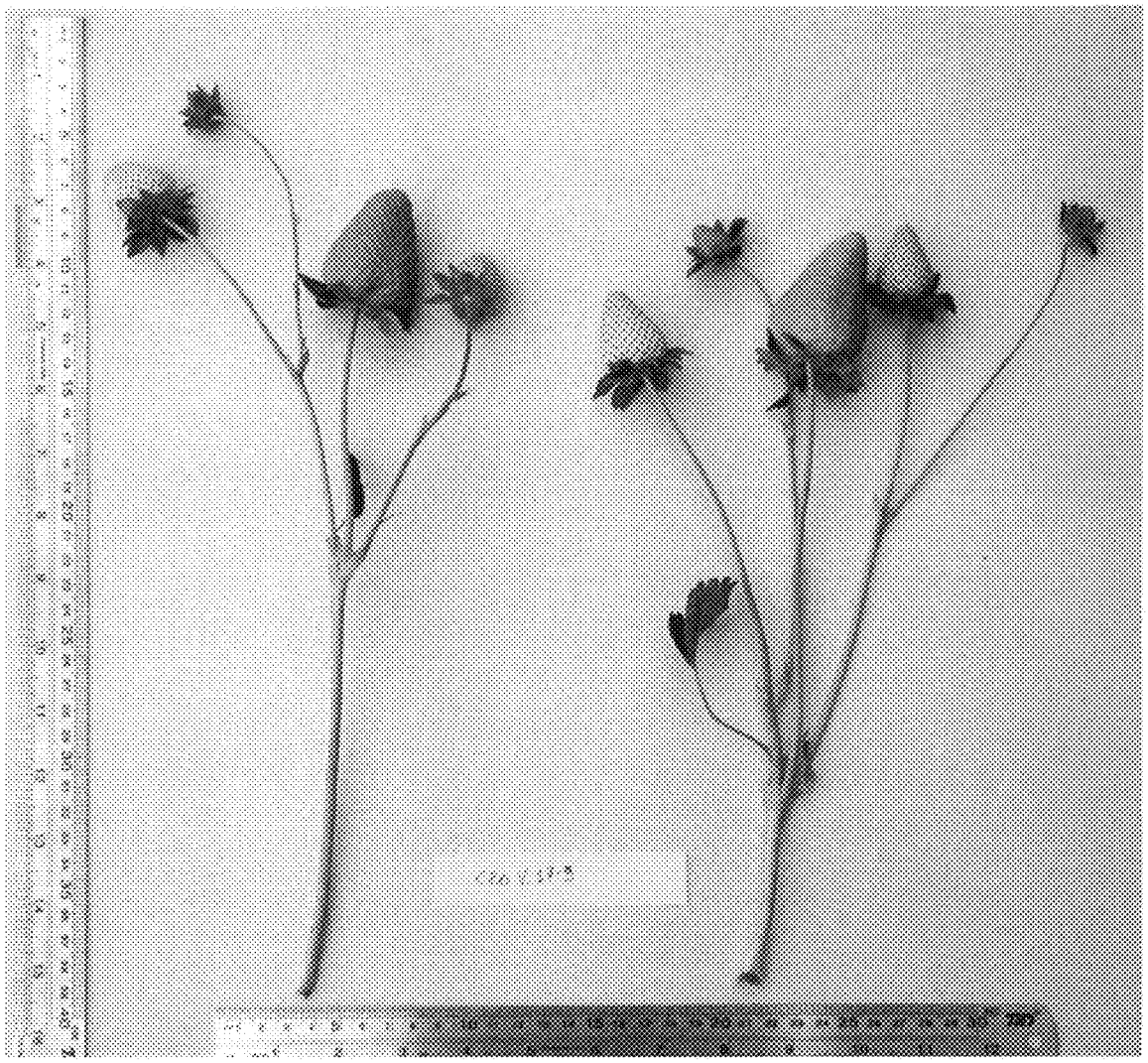

FIG. 6—illustrates a fruiting specimen of the new variety. Dimensions in centimeters and inches are included.

Figure 7:
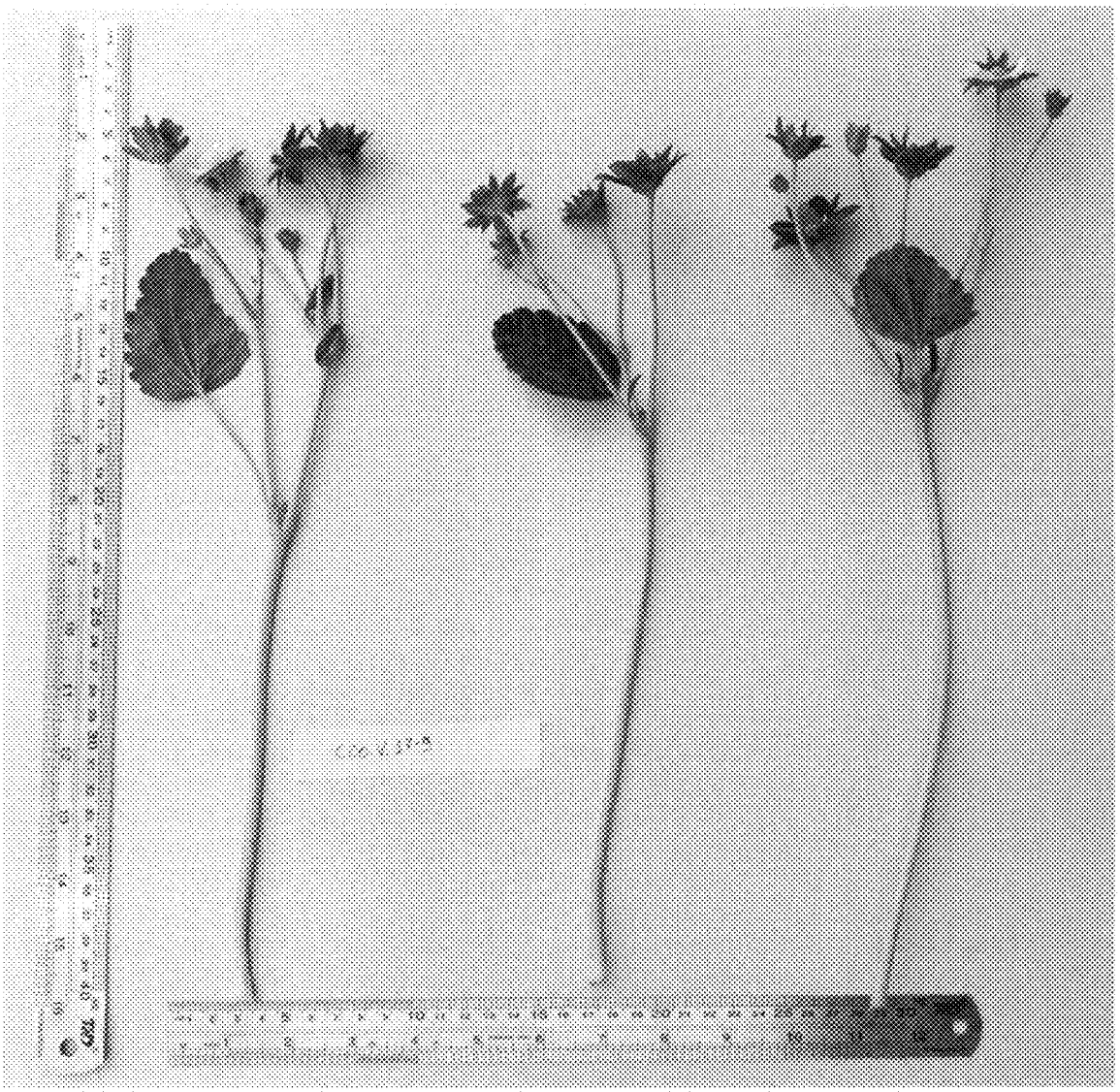

FIG. 7—illustrates a flowering specimen of the new variety. Dimensions in centimeters and inches are included.

Figure 8:
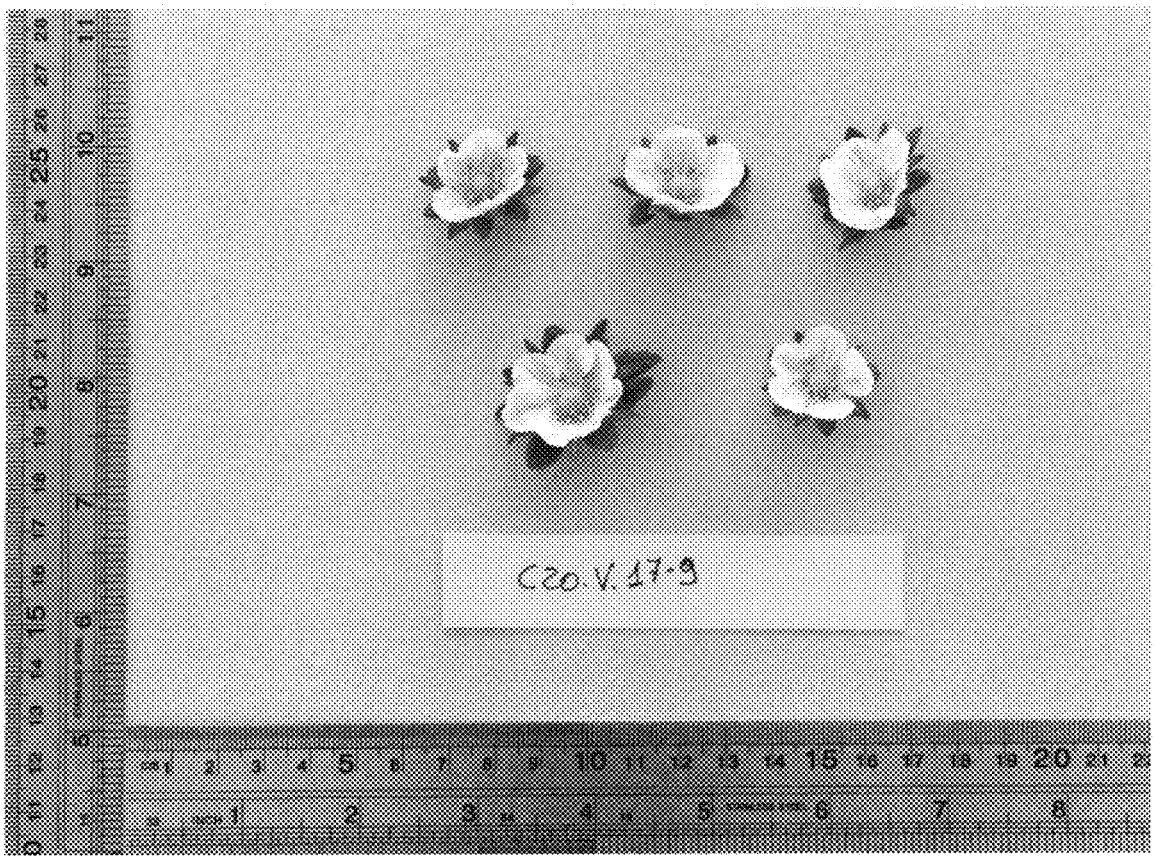

FIG. 8—illustrates flowers from the new variety, view from above. Dimensions in centimeters and inches are included.

Figure 9:
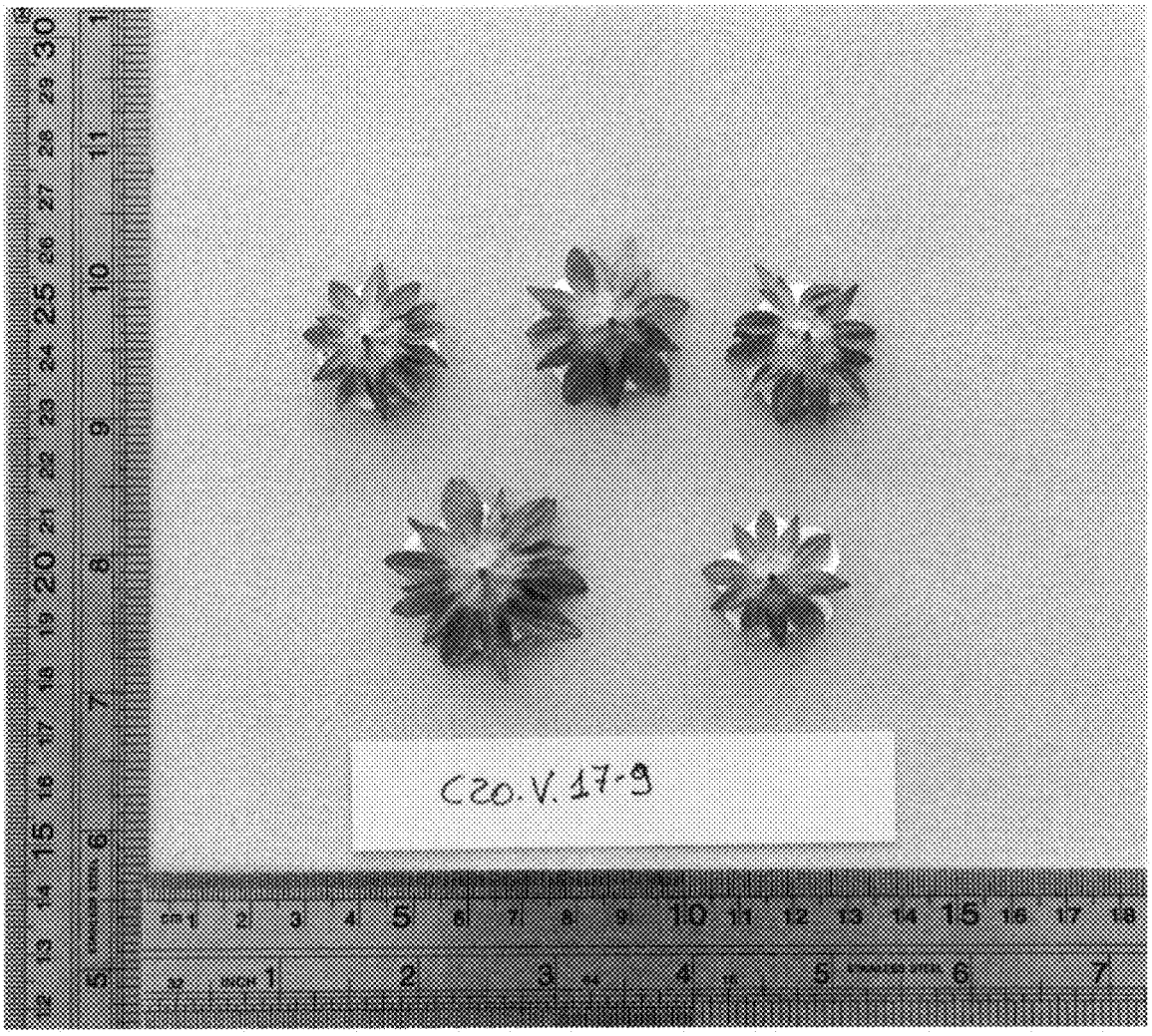

FIG. 9—illustrates specimens of the new variety's calyx, view from above. Dimensions in centimeters and inches are included.

Figure 10:
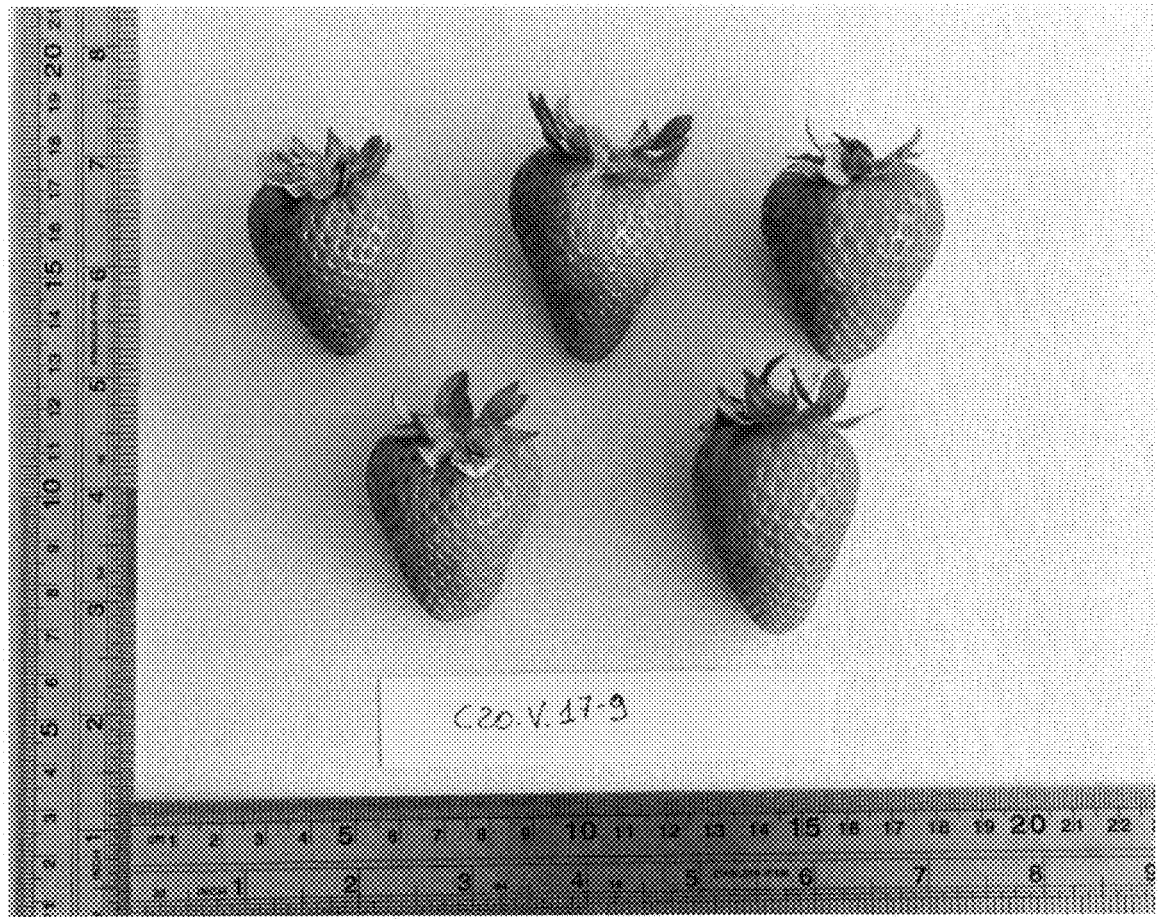

FIG. 10—illustrates specimens of the new variety's mature fruit—whole. Dimensions in centimeters and inches are included.

Figure 11:
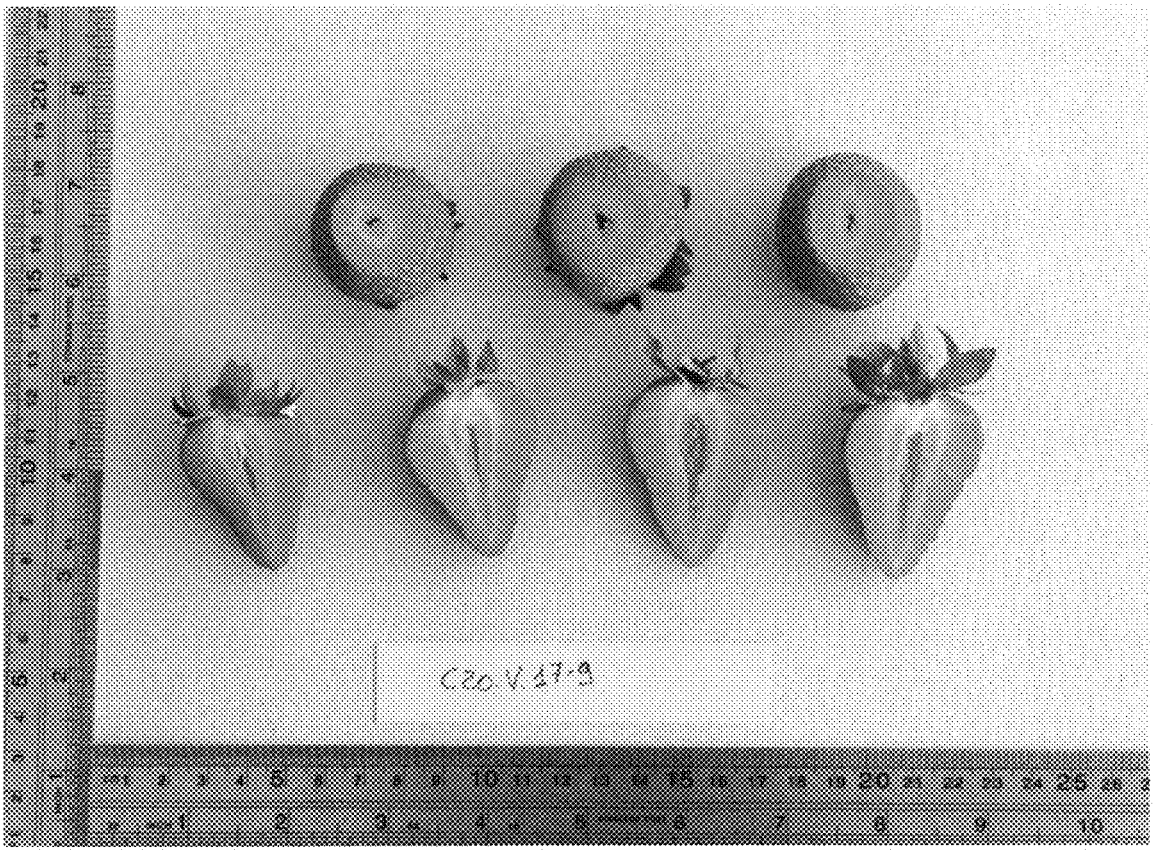

FIG. 11—illustrates specimens of the new variety's mature fruit—internal sections. Dimensions in centimeters and inches are included.

Figure 12:
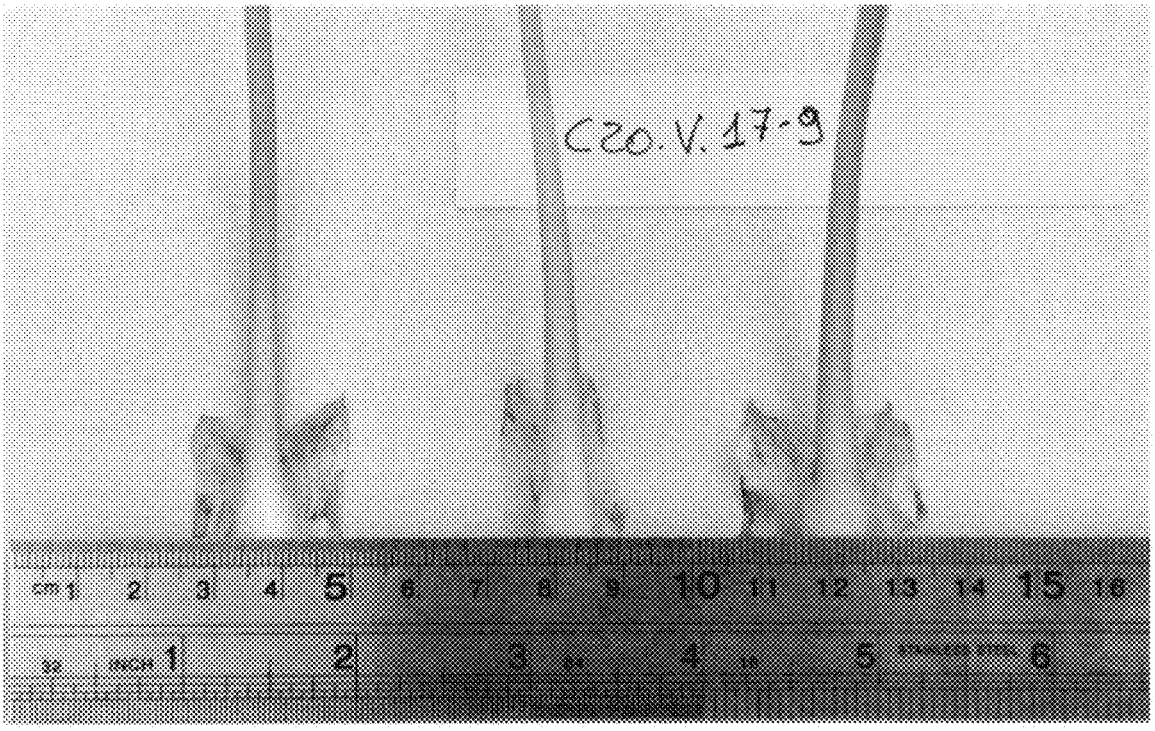

FIG. 12—illustrates specimens of the new variety's stipules—open. Dimensions in centimeters and inches are included.

DETAILED BOTANICAL DESCRIPTION

The chart used in the identification of colors is that of The Royal Horticultural Society ("R.H.S." Colour Chart), London, England, Edition V. The terminology which precedes reference to the chart has been added to indicate the corresponding color in more common terms. The detailed botanical description is based on plants which were reproduced asexually by the use of stolons in Tordesillas, Spain, located at 41° 494 N-4° 908 E, transplanted in Policoro (MT), Italy located at 40° 197 N-16° 656 E in October and grown under the cover of plastic tunnels.

The age of the plants on which the botanical description was made is between two and eight months from the transplants.

Plant:

*Type*.—Short-day.

*Configuration*.—Spreading and semi-dense.

*Vigor*.—Medium.

*Leaf*.—Length approximately from 26 cm to 29 cm, petiole and stipule included.

*Leaflets*.—Number: commonly 3. — size: medium to large in size, approximately 8 cm in length on average, and approximately 7 cm in width on average. — terminal leaflet: commonly equal in length and width, possesses a generally concave cross-section, possesses a crenate margin, and a rounded base. — blistering: commonly is high in quantity. — glossiness on the upper surface: medium. — color: variegated coloration commonly is absent; upper surface coloration commonly being near Green Group N134A and under surface commonly being near Green Group 138C. — texture (upper surface): wrinkled with small translucent waxy points and a presence of trichomes on the whole surface. — texture (lower surface): generally wrinkled with trichomes present, especially on the ribs. — venation pattern: the main transverse ribs are grafted forming an acute angle, at the insertion level of the main transverse rib there is no curvature in the initial part. The first transverse ribs, close to the base of the insertion with the petiole, have an initial curvature with a high acute angle.

*Stolons*.—High in quantity, medium pubescence in density, color is commonly near Yellow-Green Group 144D to Yellow-Green Group 145A, weak anthocyanin coloration near Red-Purple Group 59C, and the distance between plants rooted in the same stolon is approximately 26 cm to 38 cm on average.

*Petioles*.—Approximately 17 cm to 22 cm in length on average, the average minor axis and the average major axis, measured at approximately 3 cm from the base of the stipule are approximately 0.3 cm and 0.4 cm, respectively, and color is commonly near Yellow-Green Group N144C, and commonly bear generally horizontally disposed fine pubescence.

*Stipules*.—Approximately 2.9 cm to 3.3 cm in length on average, the average width of closed stipules, measured at the base of the stipule, is approximately 1.1 cm, the average width of open stipules is approximately 2.4 cm, color is near Yellow-Green 145 C with some anthocyanin coloration of near Red-Purple Group 62A.

*Floral fragrance*.—Present.

Inflorescence:

*Flowering time*.—Early, second/third week of December in Policoro (MT), Italy located at 40° 197 N-16° 656 E.

*Flower disposition*.—Above the level of the foliage.

*Flower number*.—Average, commonly 7 on average.

*Pedicel hairs*.—Pubescence generally disposed horizontally.

*Pedicel color*.—Commonly near Yellow-Green Group 144C.

*Pedicel length*.—The average length of the main and secondary pedicles measured from the base of the calyx is approximately 12 cm.

*Pedicel diameter*.—The diameter measured at approximately 2 cm from the calyx is approximately 0.2 cm.

*Flower size*.—Big, with primary flowers approximately 3.2 cm in diameter on average, and secondary flowers approximately 2.6 cm in diameter on average. Commonly the open calyx is larger than the diameter of the corolla, being approximately 3.5 cm to 4.2 cm in diameter on average.

*Petals*.—Number: approximately 6 to 7 on average. — arrangement and shape: overlapping, rounder and almost equal in length and width. — size: approximately 1.15 cm on average in both length and width. — color: near to White Group NN155C on the upper surface. — texture (upper surface): spongy texture, smooth, glabrous surface, with small translucent points; roughness at the level of insertion on the calyx. — texture (lower surface): slight roughness, which increases at the insertion with the base. Glabrous surface.

*Stamens*.—Average number: approximately 23. — average length: approximately 0.2 cm to 0.5 cm. — filament color: Yellow-Green Group 1C.

*Anthers*.—Number is approximately 22 to 24 on average and color is commonly Yellow Group 12A.

*Pollen*.—In abundance.

*Stigma*.—Shape: very jagged fan shape. — size: an average opening at approximately 400 μm. — texture: waxed dry stigma, not feathery.

*Style*.—Average length: approximately between 1800 μm. — average diameter: approximately 215 μm, which thins at the level of the insertion on the ovary, entirely crossed by a stylus channel with an average diameter of approximately 40 μm. — shape: Gynobasic style.

*Ovary*.—Superior, with slightly oval shape and average major axis and the average minor axis of approximately 700 μm and 550 μm.

*Sepals*.—Shape: generally lanceolate in configuration; attitude is commonly upwards, and generally extend beyond the petals. — number: approximately 13 to 14 on average. — size: approximately 1.4 cm to 1.6 cm in length on average, and approximately 0.6 cm to 0.8 cm in width on average at the broadest point. — color: the upper surface is commonly near Green Group 141A to 141B and the under surface is commonly near Green Group 143D. — texture (upper surface): slightly wrinkled with trichomes and translucent waxy points on the whole surface, but especially on the borders. — texture (lower surface): slightly wrinkled with trichomes on the base and on the borders.

Fruit:

*Bearing*.—Non-remontant.

*Timing*.—Medium fruiting commonly with approximately 32 to 36 days from first blooming to first fruit ripening.

*Shape*.—Conical, moderately longer than broad, commonly with a medium difference between terminal and the other fruits.

*Size*.—Large, with the primary fruit approximately 5.0 cm to 6.0 cm in length on average; approximately 3.8 cm to 4.0 cm in width on average at the broadest point; and approximately 22 grams on average.

*Surface*.—Generally uniform with strong glossiness.

*External color*.—Substantially uniform, commonly near Red Group 45B.

*Internal color*.—The flesh and the core is commonly near Orange-Red Group 33B.

*Firmness*.—Very good firmness.

*Cavity*.—Small to medium fruit cavity, as illustrated in FIG. 11.

*Achenes*.—Located generally below the fruit surface with only a narrow band where achenes are absent, and commonly near Red Group 45B in coloration.

*Calyx*.—Commonly on the same level of the fruit at the point of attachment, the calyx commonly attaches to the fruit with medium adherence, the sepals are disposed generally upwards and the fruit diameter of calyx is on the same level in relation to the diameter of fruit.

*Peduncle*.—Long, elliptical shaped in section, with the average length of the primary peduncle, measured from the base of the calyx of the primary fruit, approximately from 25 cm to 26 cm, average minor axis and the average major axis are approximately 0.4 cm and 0.5 cm respectively. The diameters of the axis are measured at approximately 3 cm from the base of the peduncle from which secondary and primary peduncles begin. The peduncle measured includes the pedicel that carries the main mature fruit and in addition the underlying peduncle. The color is commonly near Yellow-Green Group 144B to N144C.

*Pedicel*.—Commonly with pubescence extending horizontally, and color is commonly near Yellow-Green Group N144C.

*Storability*.—Medium to high.

Development:

*Fertilization*.—Self-fertile.

*Resistance to disease*.—During the time of observations and to date, no sensitivities to any disease were observed.

*Winter hardiness/cold tolerance*.—Unknown.

*Drought/heat tolerance*.—Good.

Plants of the 'NSG 9' variety have not been observed under all possible environmental conditions to date. Accordingly, it is possible that the phenotypic expression may vary somewhat with changes in light intensity and duration, cultural practices, and other environmental conditions.

SUPPLEMENTAL COMPARATIVE DATA

Hereafter, additional comparative fruit data is provided for the new variety: the 'NSG 9' variety, the 'NSG 203' variety (i.e., the female parent), the 'SIRIS' variety (i.e., the male parent) and the 'NSG 120' variety. The plants were asexually reproduced by the use of stolons in 2021 in Tordesillas, Spain located at 41° 494 N-4° 908 E, and planted in field on Oct. 18, 2021. All varieties were grown under the cover of plastic tunnels in Policoro (MT), Italy located at 40° 197 N-16° 656 E . The first pick of the fruit occurred on Jan. 15, 2022 and the last pick of the fruit occurred on May 16, 2022. The fruit were evaluated and compared on the dates indicated. Average data are followed:

TABLE 1

Accumulated Production of First Quality Fruit (g/plant)

| Variety | February 28$^{th}$ | March 30$^{th}$ | April 30$^{th}$ | May 16$^{th}$ |
|---|---|---|---|---|
| 'NSG 120' | 90 | 235 | 405 | 530 |
| 'NSG 9' | 98 | 212 | 467 | 680 |

TABLE 2

Overall Comparison of Average Fruit Weight in Policoro - Italy on year 2022

| Variety | g/fruit |
|---|---|
| 'NSG 120' | 21 |
| 'NSG 203' | 24 |
| 'SIRIS' | 21 |
| 'NSG 9' | 22 |

TABLE 3

Average Fruit Weight on Specified Dates in 2022

| Variety | March 30$^{th}$ (grams) | April 30$^{th}$ (grams) | May 16$^{th}$ (grams) |
|---|---|---|---|
| 'NSG 120' | 22 | 22 | 19 |
| 'NSG 203' | 24 | 26 | 22 |
| 'SIRIS' | 22 | 20 | 21 |
| 'NSG 9' | 22 | 23 | 21 |

TABLE 4

Fruit Analysis on May 4, 2022

| | 'NSG 120' | 'NSG 203' | 'SIRIS' | 'NSG 9' |
|---|---|---|---|---|
| Firmness (average)* | 0.57 | 0.51 | 0.67 | 0.57 |
| Dry Matter (%)** | 9.85 | 8 | 9.85 | 10.3 |
| pH (to 200) | 3.55 | 3,53 | 3.69 | 3.54 |
| Acidity as Anhydride Citric (%) | 0.48 | 0,49 | 0.46 | 0.51 |
| Soluble Solids (% Brix) | 10 | 8 | 10 | 10.5 |
| Maturity Index*** | 20.9 | 16.4 | 21.6 | 20.7 |

*Resistance to penetration measured in kilograms using a Turoni (Italy) penetrometer (20 Kg × 0.01).
**Ratio ISTISAN 1996/34 pg. 7 METHOD B.
*** MIP 160 2013 Rev.0.

I claim:

1. A new and distinct variety of strawberry plant named 'NSG 9', as illustrated and described herein.

* * * * *